(12) United States Patent
Dhumpa et al.

(10) Patent No.: US 11,131,059 B2
(45) Date of Patent: Sep. 28, 2021

(54) NANOCELLULOSE COMPOSITE SHEET FOR USE AS DERMATOLOGICAL TREATMENT OR MEDICAL DEVICE

(71) Applicant: Innovatech Engineering LLC, Tallahassee, FL (US)

(72) Inventors: Raghuram Dhumpa, Tallahassee, FL (US); Ali Darkazalli, Tallahassee, FL (US)

(73) Assignee: Innovatech Engineering LLC, Tallahassee, FL (US)

(*) Notice: Subject to any disclaimer, the term of this patent is extended or adjusted under 35 U.S.C. 154(b) by 0 days.

(21) Appl. No.: 16/947,268

(22) Filed: Jul. 27, 2020

(65) Prior Publication Data

US 2021/0148042 A1    May 20, 2021

Related U.S. Application Data

(60) Provisional application No. 62/936,322, filed on Nov. 15, 2019.

(51) Int. Cl.
*B32B 7/02*     (2019.01)
*D06M 15/05*    (2006.01)
*A61K 8/02*     (2006.01)
*A61Q 19/00*    (2006.01)
*A61K 8/73*     (2006.01)
*D06M 101/06*   (2006.01)

(52) U.S. Cl.
CPC ........... *D06M 15/05* (2013.01); *A61K 8/0208* (2013.01); *A61K 8/0212* (2013.01); *A61K 8/731* (2013.01); *A61Q 19/00* (2013.01); *A61K 2800/10* (2013.01); *A61K 2800/412* (2013.01); *D06M 2101/06* (2013.01)

(58) Field of Classification Search
CPC ............... B32B 7/02; C08J 9/28; D21C 9/001
See application file for complete search history.

(56) References Cited

U.S. PATENT DOCUMENTS

| | | | | |
|---|---|---|---|---|
| 2004/0247650 | A1* | 12/2004 | Viljanto | A61P 31/00 424/443 |
| 2014/0276513 | A1 | 9/2014 | MacDonald et al. | |
| 2016/0186377 | A1* | 6/2016 | Haldane | D21H 21/18 162/184 |
| 2017/0306055 | A1* | 10/2017 | Fan | D21C 9/007 |
| 2017/0306124 | A1* | 10/2017 | Tejado Etayo | C08B 15/05 |
| 2019/0192730 | A1 | 6/2019 | Lindgren et al. | |

FOREIGN PATENT DOCUMENTS

| | | |
|---|---|---|
| CN | 105498550 A | 4/2016 |
| KR | 20190094873 A | 8/2019 |

* cited by examiner

*Primary Examiner* — Lawrence D Ferguson
(74) *Attorney, Agent, or Firm* — American Patent Agency PC; Daniar Hussain; Xiaomeng Shi

(57) ABSTRACT

A nanocellulose composite sheet, comprising a moisturized nanocellulose material and a fabric is disclosed. The moisturized nanocellulose material and the fabric are bonded by mechanical adhesion. A method for manufacturing the nanocellulose composite sheet for use as a dermatological treatment or medical device, and an apparatus for manufacturing the nanocellulose composite sheet are also provided. The nanocellulose composite sheet has contour conformability, excellent skin-adhesion, and high capacity for moisture retention and release, and is ideal for dermatological treatments.

11 Claims, 16 Drawing Sheets

NANOCELLULOSE COMPOSITE SHEET FOR USE AS DERMATOLOGICAL TREATMENT OR MEDICAL DEVICE

CROSS-REFERENCE TO RELATED APPLICATIONS

This application is a non-provisional of and claims priority to provisional U.S. Ser. No. 62/936,322, filed on Nov. 15, 2019, entitled "Manufacture of hydrated nanocellulose sheets composited with nonwoven fabric for use as dermatological treatment or medical device," the entire disclosure of which is hereby incorporated by reference in its entirety herein.

The following related and commonly-owned patents are incorporated by reference as if fully set forth herein. U.S. Pat. No. 9,902,123 to Hipol et al., entitled "Method and apparatus for producing large uniform thickness nanomaterial sheets", issued on Feb. 27, 2018, filed on Feb. 21, 2014 as U.S. Ser. No. 14/186,795; U.S. Pat. No. 9,816,230 to Haldane et al., entitled "Formation of hydrated nanocellulose sheets with or without a binder for the use as a dermatological treatment", issued on Nov. 14, 2017, filed on Dec. 31, 2015, as U.S. Ser. No. 14/986,578; and U.S. Pat. No. 9,970,159 to Dhumpa et al., entitled "Manufacture of hydrated nanocellulose sheets for use as a dermatological treatment", issued on May 15, 2018, filed on Oct. 24, 2017 as U.S. Ser. No. 15/791,525.

NOTICE OF COPYRIGHTS AND TRADEDRESS

A portion of the disclosure of this patent document contains material which is subject to copyright protection. This patent document may show and/or describe matter which is or may become tradedress of the owner. The copyright and tradedress owner has no objection to the facsimile reproduction by anyone of the patent disclosure as it appears in the U.S. Patent and Trademark Office files or records, but otherwise reserves all copyright and tradedress rights whatsoever.

TECHNICAL FIELD

The present invention relates to the field of nanocellulose composite sheets for use, in part or in whole, as dermatological treatment or medical device products using particulate or fibrillar nanomaterials.

BACKGROUND OF THE INVENTION

The statements in the background of the invention section are provided for assistance with understanding the invention and its application and uses, and may not constitute prior art.

A plaster is a small medical dressing for minor wounds on a skin. The plaster protects the wound from bacteria and dirt in a manner that allows the skin to heal with less disturbance. Some plasters comprise antiseptic substances which are to be delivered to the skin. Some medical dressings designed as plasters comprise micronized cellulose particles among other materials.

Micronized cellulose particles in the art are comprised in a superabsorbent polymer material of a porous absorbent structure. The micronized cellulose particles become, upon drying, a porous absorbent composition, which is applied to a nonwoven material to increase its absorbency and thereby enable it to be used as a wiper for any surface including skin. However, micronized cellulose in the porous absorbent structure is a dry composition, which makes it difficult to deliver other ingredients to the skin. Nonetheless, this does not apply to plasters or medical dressings with nanocellulose.

Nanocellulose comprises cellulose nanoparticles extricated from cellulose fibers through chemical or mechanical means. Nanocellulose may be derived from wood, algae, kelp, or other terrestrial and aquatic plants, as well as bacterial sources.

Nanocellulose is similar to hydrogels and in particular to hydrogels of alginate, starch, non-nanocellulose, or other polymers, in that it retains a significant relative quantity of water. Hydrogels are often used in applications where it is necessary to maintain elevated levels of moisture saturation and/or absorption. Various hydrogels are commonly used in the manufacture of dermatological masks with or without impregnation with other dermatological agents or ingredients. Application of hydrogel masks infused with dermatological agents onto a user's skin creates an interface for transfer of dermatological active ingredients. Unfortunately, such masks using established hydrogel formulations tend to have poor contour conformability, inadequate skin adhesion, and limited transfer efficiency of active ingredients to the skin.

A medical dressing in the art comprises a carrier material and a composite material. The composite material comprises oil droplets dispersed in a matrix. The matrix comprises one or more cellulose derivatives and nanocellulose. The carrier material is in the form of a gel, such as a hydrogel. Such conventional hydrogels require bonding through chemical, thermal, or solvent processes, and thus are not optimized for efficient high-volume sheet production, uniform infusion of active ingredients, or controlled porosity.

Therefore, there is a clear and present need to develop a moisturized nanocellulose composite sheet that is capable of absorbing and releasing significant quantities of dermatological agents to the skin and is also optimized for efficient high-volume sheet production.

It is against this background that the present invention was developed.

BRIEF SUMMARY OF THE INVENTION

This summary is provided to introduce a selection of disclosed concepts in a simplified form that are further described below in the detailed description including the drawings provided. This summary is not intended to identify key features or essential features of the claimed subject matter. Nor is this summary intended to be used to limit the claimed subject matter's scope.

In one aspect, one embodiment of the present invention is a nanocellulose composite sheet comprising a moisturized nanocellulose material and a fabric, wherein the moisturized nanocellulose material and the fabric are bonded by mechanical adhesion. The nanocellulose composite sheet shows several advantageous properties. These properties include high conformability, drape-ability, large surface area, good levels of adhesion to the skin of a user, ability to contain and effectively deliver nano- and micro-particles, high porosity, and high rate of evaporation of water from the sheet. These properties make the nanocellulose sheet ideal for resting against the skin of a user and delivering dermatological agents which are generally difficult to do, or which require multi-step processes to be delivered to the skin.

Accordingly, one embodiment is a nanocellulose composite sheet, comprising a moisturized nanocellulose material and a fabric, where the moisturized nanocellulose material and the fabric are bonded by mechanical adhesion.

In some embodiments, the moisturized nanocellulose material comprises nanocellulose and water, where the nanocellulose is between 10 and 12 weight % of the nanocellulose composite sheet, and where the water is between 76 and 80 weight % of the nanocellulose composite sheet.

In some embodiments, the fabric is viscose, and the viscose is between 10 and 12 weight % of the nanocellulose composite sheet.

In some embodiments, the moisturized nanocellulose material comprises at least one element selected from the group consisting of cellulose nanocrystals, cellulose nanofibers, nano-fibrillated cellulose, and bacterial nanocellulose.

In some embodiments, the moisturized nanocellulose material comprises a plurality of cellulose fibrils with a width between 5 and 20 nanometers and a length between 1 and 10 micrometers.

In some embodiments, the moisturized nanocellulose material comprises crystalline and rigid nanoparticles.

In some embodiments, the crystalline and rigid nanoparticles have a length between 100 and 1,000 nanometers.

In some embodiments, the fabric comprises an element selected from the group consisting of yarn and thread.

In some embodiments, the fabric is selected from the group consisting of a woven fabric and a non-woven fabric.

In some embodiments, the fabric is selected from the group consisting of a synthetic fabric, a non-synthetic fabric, and a plastic.

In some embodiments, the fabric is a non-woven fabric selected from the group consisting of a synthetic fabric, a semi-synthetic fabric, and a non-synthetic fabric.

In some embodiments, the fabric is a viscose fabric having a grammage of about 40 g/m$^2$.

In some embodiments, the moisturized nanocellulose sheet has a nanocellulose concentration between 5 weight % and 25 weight %.

In some embodiments, the moisturized nanocellulose material is a hydrated nanocellulose material.

In some embodiments, the nanocellulose composite sheet further comprises a flexible non-woven protective covering.

Yet another embodiment of the present invention is a method of manufacturing a nanocellulose composite sheet, comprising a moisturized nanocellulose material and a fabric, where the moisturized nanocellulose material and the fabric are bonded by mechanical adhesion, the method comprising the steps, providing a diluted nanocellulose suspension; dispersing the diluted nanocellulose suspension onto the fabric; and partially drying the diluted nanocellulose suspension until the diluted nanocellulose suspension is transformed to the moisturized nanocellulose material bonded to the fabric by mechanical adhesion to form the nanocellulose composite sheet.

In some embodiments, the moisturized nanocellulose material is infused with one or more active ingredients for dermatological and/or cosmetic formulations for the transfer of said active ingredients onto skin.

In some embodiments, the active ingredients are selected from the group consisting of hyaluronic acid, hyaluronic acid derivatives, collagen, collagen derivatives, Niacin, tocopherols, ascorbic acid, vitamin-antioxidants, botanical extracts, and biological materials, where the biological materials are derived from the group consisting of plant, animal, and microbial sources.

In some embodiments, the diluted nanocellulose suspension comprises a purified nanocellulose aqueous gel diluted in a suspension medium.

In some embodiments, the diluted nanocellulose suspension has a nanocellulose concentration between 0.1 weight % to 3 weight %.

In some embodiments, the partially drying the moisturized nanocellulose material is performed by applying heat, where the heat is applied by an element selected from the group consisting of thermal convection, thermal conduction, thermal radiation, heat transfer by chemical conversion, and phase change.

In some embodiments, the partially drying the moisturized nanocellulose material is performed by applying a vacuum differential, where pressure of the vacuum differential is increased until drying occurs at a maximal rate.

In some embodiments, the partially drying the diluted nanocellulose suspension until the diluted nanocellulose suspension is transformed to a moisturized nanocellulose material is done until a water content of the moisturized nanocellulose material is between 60 and 90 weight %.

Yet another embodiment of the present invention is an apparatus for manufacturing a nanocellulose composite sheet comprising a moisturized nanocellulose material and a fabric, where the moisturized nanocellulose material and the fabric are bonded by mechanical adhesion, the apparatus comprising a suspension dispenser for dispersing a diluted nanocellulose suspension onto the fabric; and a dryer for partially drying the diluted nanocellulose suspension to the moisturized nanocellulose material.

Additional aspects of the disclosed embodiments will be set forth in part in the description which follows, and in part will be clear from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. For clarity, simplicity, and flexibility, not all elements, components, or specifications are defined in all drawings. Not all drawings corresponding to specific steps or embodiments of the present invention are drawn to scale. Emphasis is instead placed on illustration of the nature, function, and product of the manufacturing method and devices described herein.

DETAILED DESCRIPTION

In the following description, for purposes of explanation, numerous specific details are set forth in order to provide a thorough understanding of the invention. It will be apparent, however, to one skilled in the art that the invention can be practiced without these specific details. In other instances, structures, devices, activities, methods, and processes are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

One embodiment of the present invention relates to a nanocellulose composite sheet with a moisturized nanocellulose material bonded to a fabric by mechanical adhesion.

The term "moisturized" means that the nanocellulose material comprises a fluid selected from the group consisting of water, alcohol, and oil. In some embodiments, the nanocellulose material is moisturized with water, and the term "hydrated" may be used instead. Therefore, in such a case, the nanocellulose composite sheet is hydrated and the moisturized nanocellulose material is a hydrated nanocellulose material.

Nanocellulose refers to nano-structured cellulose, where at least one dimension of a cellulose particle is measured in nanometers or in the nanometer scale. In some embodiments, the nanocellulose is exfoliated from cellulose fibrils via mechanical or chemical processes, and may be derived from many sources including bacteria, plant, wood, algae and even fruit waste. For example, the nanocellulose may be extracted from wood pulp cellulose. Pre-treatments may be used, such as TEMPO-mediated oxidation, and the nanocellulose composite sheet 100 may be formed by using TEMPO-oxidized nano-cellulose.

Dimension and Cross Section of the Nanocellulose Composite Sheet

Figure 1A:
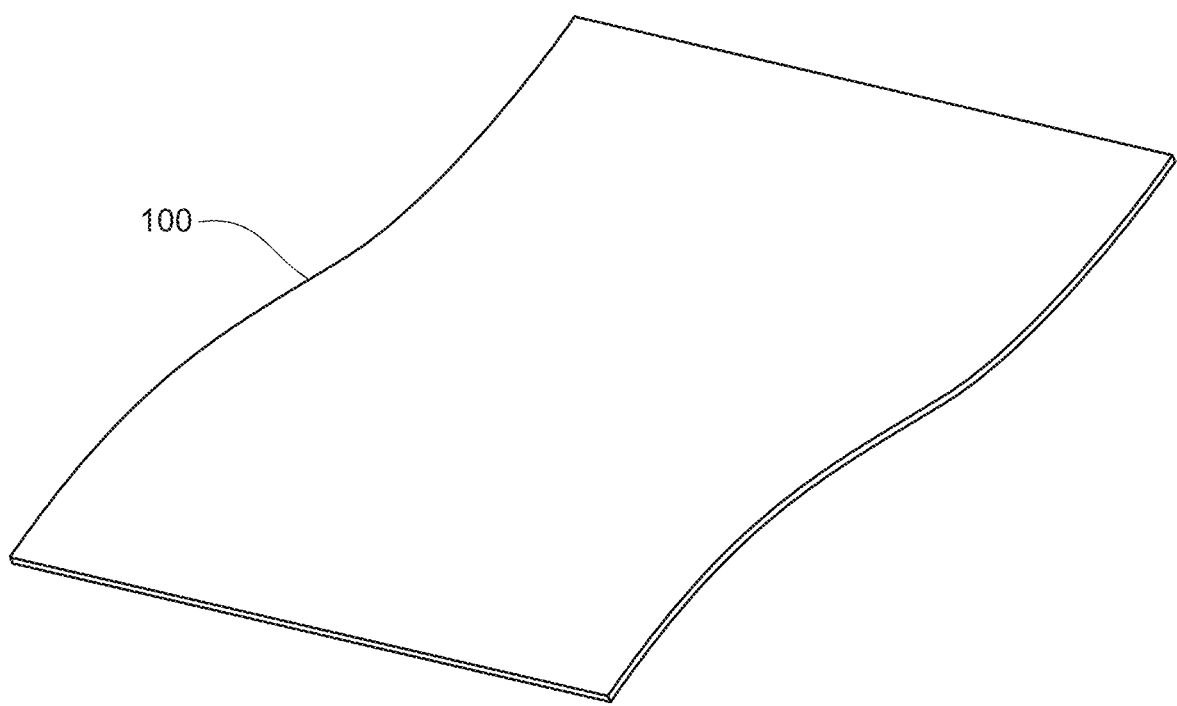
FIG. 1A shows a perspective view of a nanocellulose composite sheet according to one embodiment of the present invention.
Figure 1B:
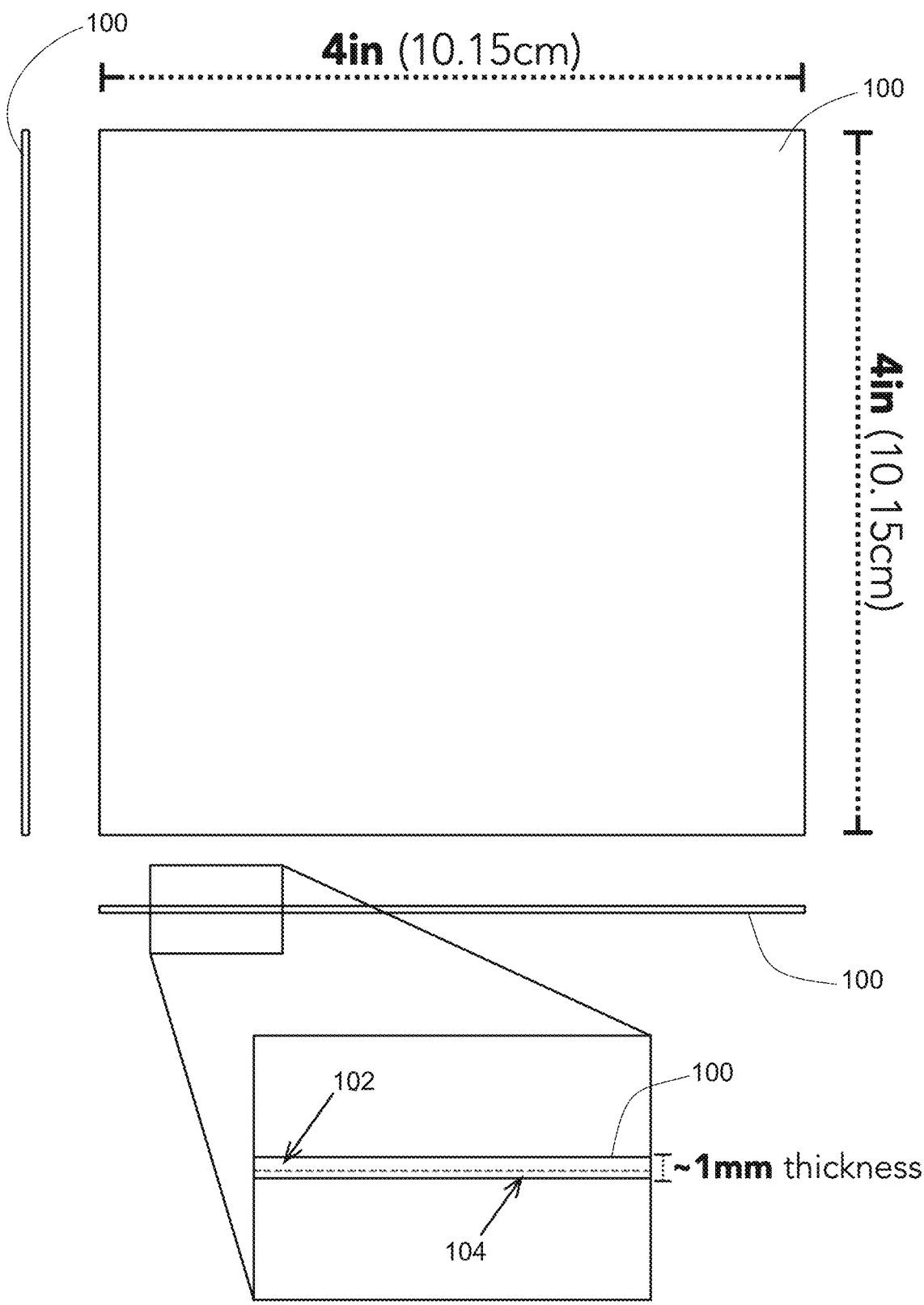
FIG. 1B shows a frontal top view the nanocellulose composite sheet of FIG. 1A according to one embodiment of the present invention.
Figure 1C:
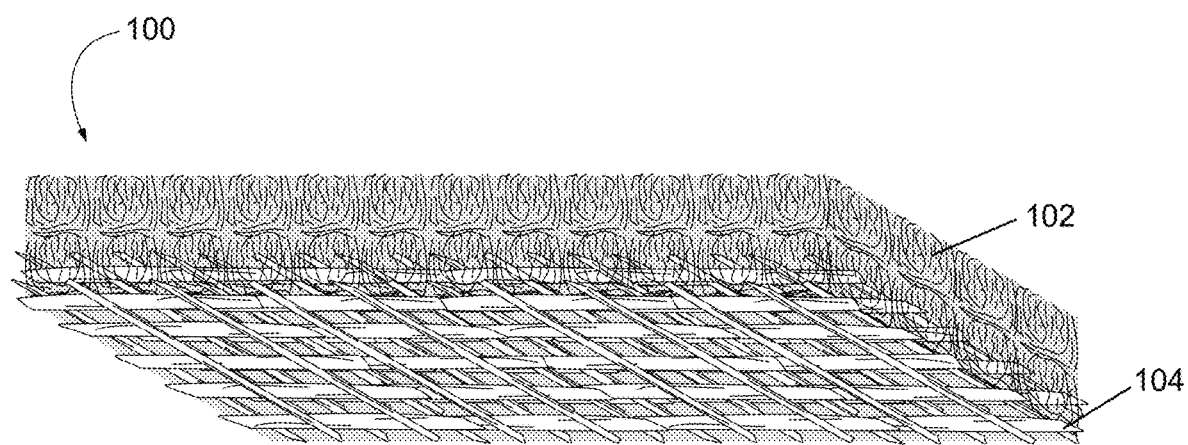
FIG. 1C shows a magnified cross-sectional view of the nanocellulose composite sheet of FIG. 1A according to one embodiment of the present invention.

FIGS. 1A, 1B, and 1C illustrate the nanocellulose composite sheet and its dimensions and a magnified cross section of the nanocellulose composite sheet, respectively.

FIG. 1A is a perspective view of a nanocellulose composite sheet 100 according to one embodiment of the present invention. In one embodiment, the nanocellulose composite sheet 100 may be manufactured in a manner that its tensile strength is approximately 1.17 N/mm$^2$±0.25 N/mm$^2$. The nanocellulose composite sheet 100 is preferably a stand-alone medical, cosmetic, or dermatological moisturizing device.

FIG. 1B shows a frontal top view of the nanocellulose composite sheet of FIG. 1A. In one embodiment, the nanocellulose composite sheet 100 is square shaped with a length between 9 and 11.5 centimeters (between 3.5 and 4.5 inches). FIG. 1B also shows a magnification of the cross section of the nanocellulose composite sheet 100. The magnification shows a moisturized nanocellulose material 102 bonded to a fabric 104. In one embodiment, the overall thickness of the nanocellulose composite sheet 100 is 0.75 to 1.25 millimeters (between 0.03 and 0.05 inches).

The moisturized nanocellulose material may comprise at least one nanocellulose material selected from the group consisting of cellulose nanocrystal (CNC or NCC), cellulose nanofibers (CNF), nano-fibrillated cellulose (NFC), and bacterial nanocellulose. Bacterial nanocellulose is nano-structured cellulose produced by bacteria. Cellulose nanofibers (CNF) comprise nanosized cellulose fibrils with a high length to width ratio. Nanosized cellulose fibrils may have a width between 5 and 20 nanometers and a length between 1 and 10 micrometers. Cellulose fibrils are pseudo-plastics with thixotropy. Thixotropy leads to cellulose fibrils showing high viscosity under normal conditions but low viscosity when shaken or agitated. After shaking, the cellulose fibrils may regain much of their original high viscosity. The moisturized nanocellulose material may also comprise highly crystalline and rigid nanoparticles, with a length of preferably 100 to 1,000 nanometers. These nanoparticles may be obtained from native fibers by acid hydrolysis.

The nanocellulose concentration in the moisturized nanocellulose material may be between 5 weight % to 25 weight % of the moisturized nanocellulose material. For example, in one embodiment, the moisturized nanocellulose material may comprise nanocellulose and water, where the nanocellulose is between 10 and 12 weight % of the nanocellulose composite sheet, and the water is between 76 and 80 weight % of the nanocellulose composite sheet.

Generally, a fabric is a material with a network of natural or artificial fibers. The term fabric is used in this disclosure as a synonym to the term textile according to the present invention. In some embodiments, the fabric in the nanocellulose composite sheet comprises yarn and/or thread. In some embodiments, the fabric is a woven, or a non-woven fabric, and may comprise synthetic fabric, non-synthetic fabric, or plastic. In some embodiments, the fabric is a non-woven viscose having a grammage between 35 and 45 gsm (g/m$^2$), and may be a synthetic fabric, a semi-synthetic fabric, or a non-synthetic fabric. In some embodiments, the viscose may be between 10 and 12 weight % of the nanocellulose composite sheet.

FIG. 1C shows an interface between the moisturized nanocellulose material 102 and the fabric 104 in a greater magnification compared to the magnification of the cross section of the nanocellulose composite sheet 100 in FIG. 1B. That is, FIG. 1C is a magnified cross-sectional view of the nanocellulose composite sheet 100 of FIG. 1B in greater detail. The magnification shows the mechanical adhesion of the moisturized nanocellulose material 102 to the fabric 104.

Mechanical adhesion refers to a process leading to a state where the moisturized nanocellulose material 102 fills the spaces among fibers of the fabric 104 in a manner that the moisturized nanocellulose material 102 and the fabric 104 are interwoven. Therefore, mechanical adhesion leads to stronger van der Waals forces forming a large-area bond. Even a tiny amount of mechanical adhesion can increase the van der Waals bonds between the moisturized nanocellulose material 102 and the fabric 104 by an order of magnitude. In one embodiment, a peak break force of the nanocellulose composite sheet 100 is 5.58±0.53N. The peak break force and tensile strength depend on the percentage of the nanocellulose in the moisturized nanocellulose material, and the fabric.

The nanocellulose composite sheet 100 may be cut into different forms, including different shapes, sizes or configurations that facilitate direct application to the skin. The different shapes and sizes may be used for different skin contact applications on different parts of a user's body. Exemplary applications include, but are not limited to, cosmetic, dermatological, and medical devices. FIGS. 2 to 6 and corresponding discussions illustrate exemplary shapes that may be cut from the nanocellulose composite sheet 100. The following discussion should not, however, limit the scope of the applications of the invention.

Exemplary Embodiments: Different Shaped Masks Cut from Nanocellulose Composite Sheets FIGS. 2 to 6 illustrate different masks cut from the nanocellulose composite sheet for application on different parts of the skin.

Figure 2:
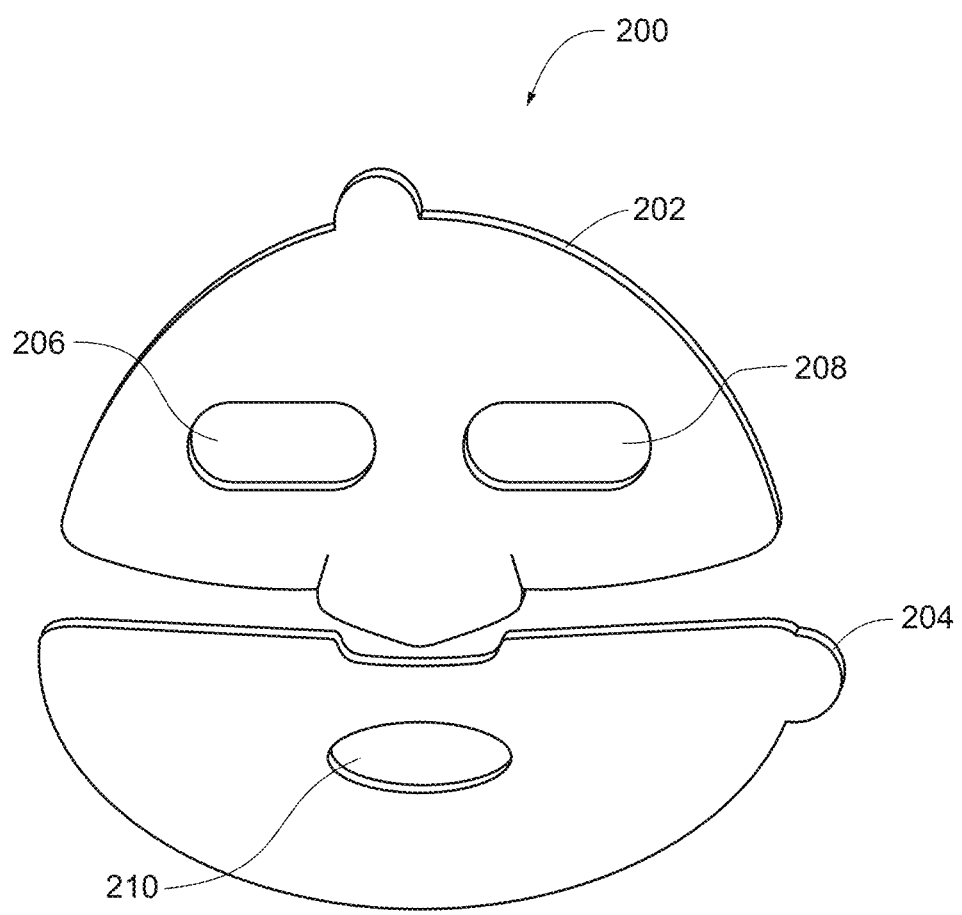
FIG. 2 shows a perspective view of a facial mask cut from the nanocellulose composite sheet of FIG. 1A according to one embodiment of the present invention.

FIG. 2 shows a facial mask 200 cut from the nanocellulose composite sheet of FIG. 1A. The facial mask 200 comprises an upper part 202 for covering an upper half of a user's face and a lower part 204 for covering a lower half of the face. When applied onto the user's face, the moisturized nanocellulose material may be in direct contact with the skin for delivery of one or more active ingredients.

More specifically, the upper part 202 of the facial mask 200 comprises a left hole 206 and a right hole 208. Once the upper half of a user's face is covered with the upper part 202 of the facial mask 200, the user can see through the left and right holes 206, and 208. The lower part 204 of the facial mask 200 comprises a mouth hole 210. Once the lower half of a user's face is covered by the lower part 204 of the facial mask 200, the user can speak through the mouth hole 210.

The facial mask 200 is able to conform to the facial contour, enabling full coverage of all exposed facial skin. In some embodiments, the facial mask 200 provides an even dispersion of dermatologically active ingredients tailored to a specific dermatological purpose, while allowing fast transpiration or evaporation of water through the moisturized nanocellulose material and the fabric, leading to a dynamic fluid and nutrient delivery system between the moisturized nanocellulose material and the skin beneath. In some embodiments, the dermatologically active ingredients are particulate or solution-based and may provide medicated or nutritional supplements to the skin.

Figure 3:
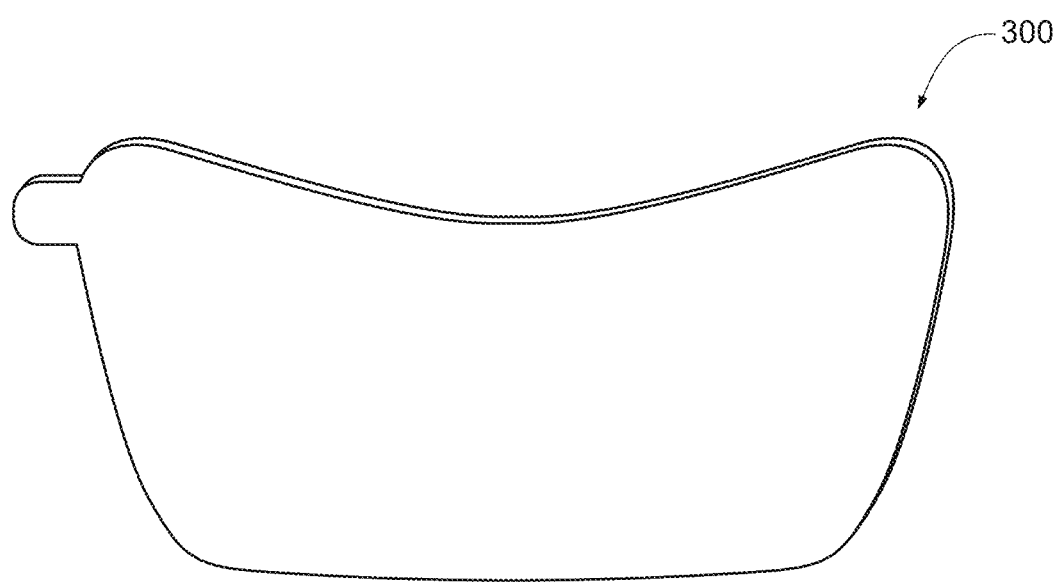
FIG. 3 shows a perspective view of a neck mask cut from the nanocellulose composite sheet of FIG. 1A according to one embodiment of the present invention.

FIG. 3 shows a neck mask 300 cut from the nanocellulose composite sheet of FIG. 1A. The neck mask 300 is configured to be wrapped around the neck of a user.

Figure 4:
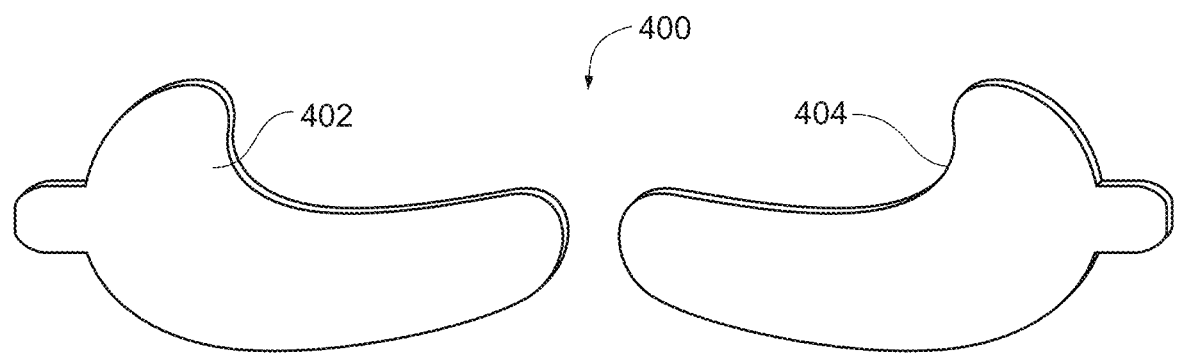
FIG. 4 shows a perspective view of eye masks cut from the nanocellulose composite sheet of FIG. 1A according to one embodiment of the present invention.

FIG. 4 shows an eye mask 400 cut from the nanocellulose composite sheet of FIG. 1A. The eye mask 400 comprises a left part 402 and a right part 404. The eye mask 400 is cut in a shape where the left part 402 fits under the left eye and the right part 404 fits under the right eye of a user.

Figure 5:
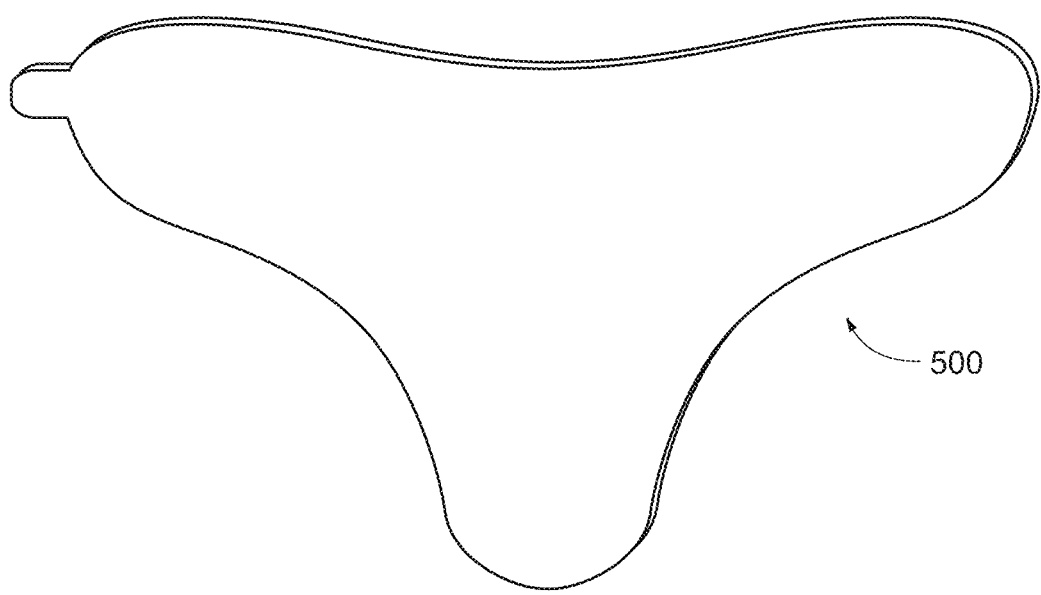
FIG. 5 shows a perspective view of a chest mask cut from the nanocellulose composite sheet of FIG. 1A according to one embodiment of the present invention.

FIG. 5 shows a chest mask 500 cut from the nanocellulose composite sheet of FIG. 1A, that fits on a chest of a user.

Figure 6:
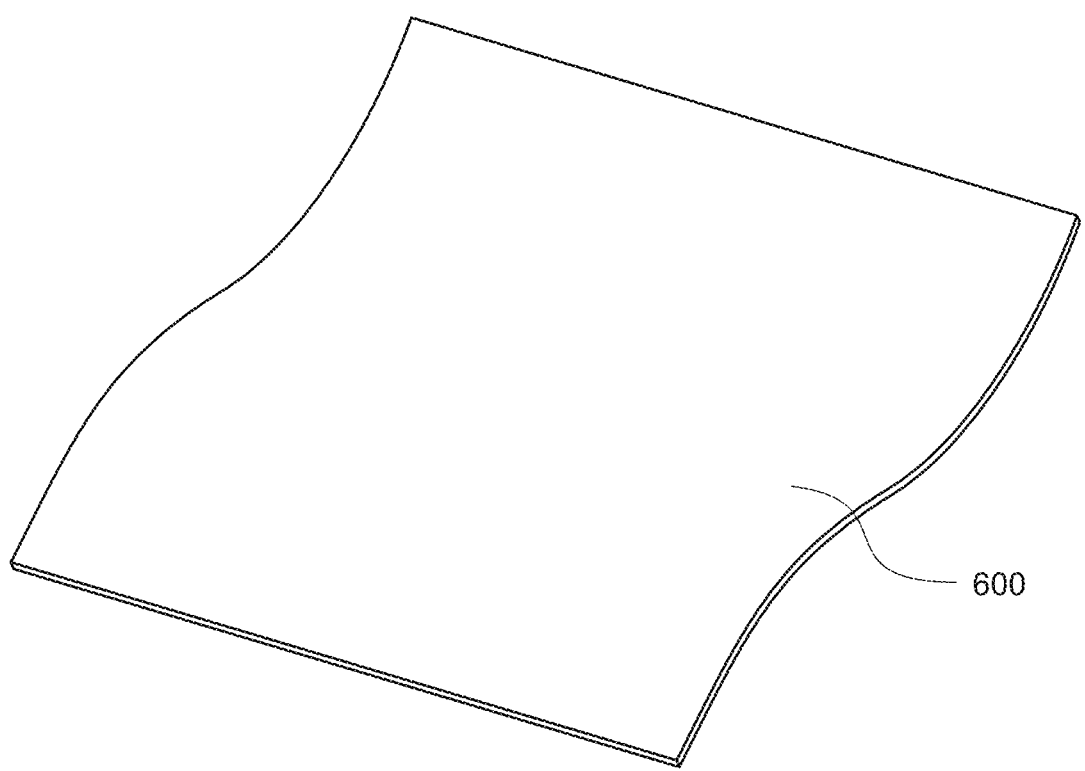
FIG. 6 shows a perspective view of a multi-use square mask cut from the nanocellulose composite sheet of FIG. 1A according to one embodiment of the present invention.

FIG. 6 shows a multi-use square mask 600 cut from the nanocellulose composite sheet of FIG. 1A. The multi-use square mask 600 may be applied to sides of a user's mouth, nose, eyes, temples, cheeks, jaws, or any other locations on a user's face or body. Similarly, shoulder masks, back masks, thigh masks, and masks of other shapes may be cut from the multi-use square mask 600 in any desirable form, including any desired shape, size, and configuration.

Figure 7:
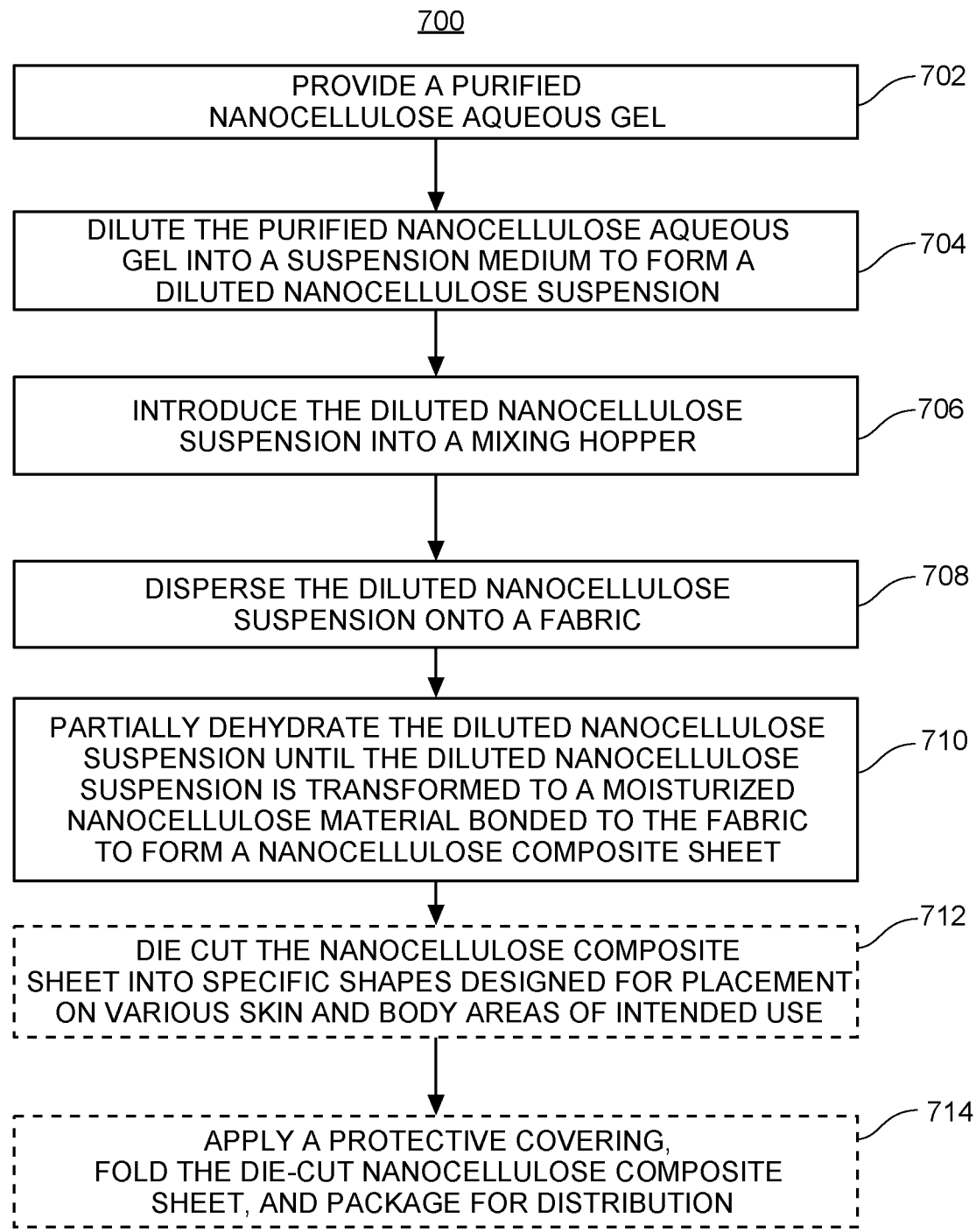
FIG. 7 shows a flow diagram describing the steps of manufacturing the nanocellulose composite sheet of FIG. 1A according to one embodiment of the present invention.
Figure 8:
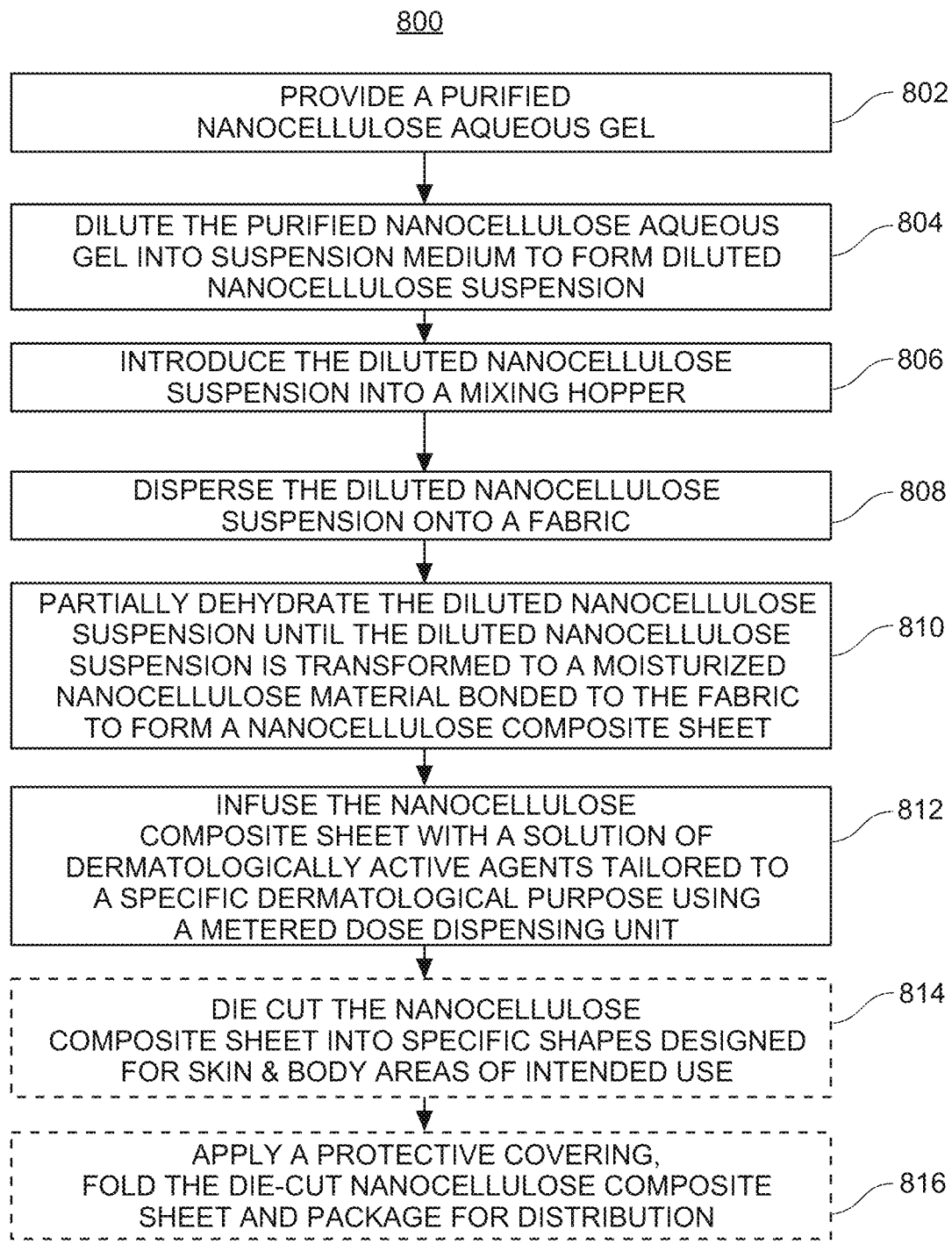
FIG. 8 shows a flow diagram describing the steps of manufacturing the nanocellulose composite sheet of FIG. 1A infused with a solution of dermatological agents, active ingredients, or other cosmetic or medicinal adjuncts according to one embodiment of the present invention.

As disclosed herein, the nanocellulose composite sheet of FIG. 1A is produced by carrying out a series of steps, which are described in FIGS. 7 and 8.

Manufacturing the Nanocellulose Composite Sheet

Another embodiment of the present invention relates to a method of manufacturing the nanocellulose composite sheet, as illustrated in the flow diagrams of FIGS. 7 and 8.

FIG. 7 shows a flow diagram 700 describing the steps of manufacturing a nanocellulose composite sheet according to one embodiment of the present invention. At a step 702, a purified nanocellulose aqueous gel is provided. In some embodiments, the purified nanocellulose aqueous gel comprises nanocellulose fibers, nanocellulose crystals, or a combination of both in a controlled proportion, where the fibers and/or crystals have an average diameter between 5 to 100 nm and an average length up to 10 microns.

At a step 704, the purified nanocellulose aqueous gel is diluted in a suspension medium to form a diluted nanocellulose suspension. In some embodiments, the diluted nanocellulose suspension comprises a nanocellulose concentration between 0.1 weight % and 3 weight %. Exemplary suspension media include, but are not limited to, water, alcohols, or oil, where an oil-based suspension medium may further comprise a surfactant.

In some embodiments, various additives may be dissolved or dispensed into the diluted nanocellulose suspension in controlled steps or sequences. Such additives include, but are not limited to, binding agents, cross-linking agents, dermatologically active ingredients, morphology-altering particles, base material modifiers, pure nanocellulose crystals, polyelectrolytes, and pH modifying solutions.

In some embodiments, pure nanocellulose crystals may be dissolved or dispensed into the diluted nanocellulose suspension, to increase the overall strength of the nanocellulose composite sheet, making it less likely to tear, while reducing the drying time. It is desirable for the diluted nanocellulose suspension to show a high level of moisture. Conventionally, crystals are not used in the manufacture of nanocellulose sheets, because they do not swell in the presence of a solution with a nanocellulose aqueous gel. Embodiments of the present invention carefully balance the use of nanocellulose crystals and nanocellulose fibers to achieve desired moisture levels in the nanocellulose sheet, while enhancing the durability and tensile strength and reducing overall processing times of manufacturing the nanocellulose sheet.

The dilution of the purified nanocellulose aqueous gel into a suspension medium and subsequent usage of such a diluted nanocellulose suspension in the manufacture of the nanocellulose composite sheet is beneficial as it allows the purified nanocellulose aqueous gel to be accepted from multiple sources. For example, grown pellicles of nanocellulose may be obtained in bacterially grown cellulose.

In some embodiments, the purified nanocellulose aqueous gel is pre-treated before nanocellulose formation from cellulose fibers. Such pre-treatments may include mechanical or enzymatic treatment of a cellulose containing material. For example, cellulose containing material may be oxidized using 2,2,6,6-tetramethylpiperidin-1-oxyl radical ("TEMPO"), which introduces charged groups. Carboxymethylation may also be used to pre-treat the cellulose containing material. Finally, acid hydrolysis may be used to treat the cellulose containing material.

Next, at a step 706, the diluted nanocellulose suspension is introduced into a mixing hopper. In step 708, the mixing hopper disperses the diluted nanocellulose suspension onto a fabric. In some embodiments, the fabric may be a woven fabric instead.

Thereafter, in a step 710, a vacuum differential is applied to partially dry the diluted nanocellulose suspension until the diluted nanocellulose suspension is transformed to a moisturized nanocellulose material bonded to the fabric by mechanical adhesion to form the nanocellulose composite sheet.

In some embodiments, the nanocellulose composite sheet may be supported by a secondary inert filter. This secondary inert filter may be used to support or contain the fabric during the manufacture of the nanocellulose composite sheet. The non-woven fabric may only be in temporary contact with this secondary inert filter during the manufacturing process.

In some embodiments, additive ingredients may be applied to the nanocellulose composite sheet, via mechanisms such as spraying, dipping, soaking, and the like. Such additives include, but are not limited to, binding agents, cross-linking agents, dermatologically active ingredients, morphology-altering particles, base material modifiers, pure nanocellulose crystals, polyelectrolytes, and pH modifying solutions.

In an optional step 712, the nanocellulose composite sheet is cut by rotary die cutter into specific shapes designed for placement on various skin and body areas of intended use. Finally, in an optional step 714, a non-woven protective covering is applied onto the nanocellulose composite sheet and the nanocellulose composite sheet is subsequently folded and packaged for distribution.

FIG. 8 is a flow diagram 800 describing the steps of manufacture of a nanocellulose composite sheet infused with a solution of dermatological agents, active ingredients, or other cosmetic or medicinal adjuncts according to one embodiment of the present invention. More specifically, similar to the process shown in FIG. 7, a purified nanocellulose aqueous gel is provided at a step 802. In some embodiments, the purified nanocellulose aqueous gel comprises nanocellulose fibers, nanocellulose crystals, or a combination of both in a controlled proportion. Embodiments of the present invention may utilize nanocellulose fibers and/or crystals having any diameter and length. For example, the nanocellulose fibers and/or crystals may have a diameter between 5 to 100 nm and a length up to 10 microns.

Next, at a step 804, the purified nanocellulose aqueous gel is diluted into a suspension medium to form a diluted nanocellulose suspension. Exemplary suspension media include, but are not limited to, water, alcohols, or oil, where the oil-based suspension medium may further comprise a surfactant. Similar to in the method described in FIG. 7, the diluted nanocellulose suspension may have a nanocellulose concentration between 0.1 weight % to 3 weight %.

Next, at a step 806, the diluted nanocellulose suspension is introduced into a mixing hopper. In step 808, the mixing hopper disperses the diluted nanocellulose suspension onto the fabric. Thereafter, in a step 810, a vacuum differential is applied to dry the diluted nanocellulose suspension to a moisturized nanocellulose material bonded to the fabric by mechanical adhesion to form the nanocellulose composite sheet. In some embodiments, the nanocellulose composite sheet is supported by a secondary inert filter similar to the method described in FIG. 7. The nanocellulose composite sheet has a nanocellulose concentration between 5 weight % to 25 weight %.

In an optional step 812, subsequent infusion of the nanocellulose composite sheet with a solution of dermatologically active agents tailored to a specific dermatological purpose using a metered dose dispensing unit is performed. This step of manufacture is used to yield a nanocellulose composite sheet impregnated with specific dermatological agents, drugs, or active ingredients tailored to specific medical indications. This step of manufacture is used to yield a nanocellulose composite sheet infused with selected dermatological or cosmetic formulations designed for specific dermatological or cosmetic purposes, and for the transfer of said formulation ingredients from the nanocellulose composite sheet onto the skin at the intended area of use.

In some embodiments, the active ingredients are selected from the group consisting of hyaluronic acid, hyaluronic acid derivatives, collagen, collagen derivatives, Niacin, tocopherols, ascorbic acid, vitamin-antioxidants, botanical extracts, and biological materials, where the biological materials are derived from the group consisting of plant, animal, and microbial sources.

In another optional step 814, the nanocellulose composite sheet is cut by a rotary die cutter into specific shapes designed for placement on various skin and body areas of intended use. Finally, in an optional step 816, a non-woven protective covering is applied onto the nanocellulose composite sheet and subsequently the nanocellulose composite sheet is folded and packaged for distribution.

Apparatus for Manufacturing the Nanocellulose Composite Sheet

Another embodiment of the present invention relates to an apparatus for manufacturing the nanocellulose composite sheet. FIGS. 9 to 12 show the apparatus for manufacturing the nanocellulose composite sheet and magnified views of different parts thereof.

Figure 9:
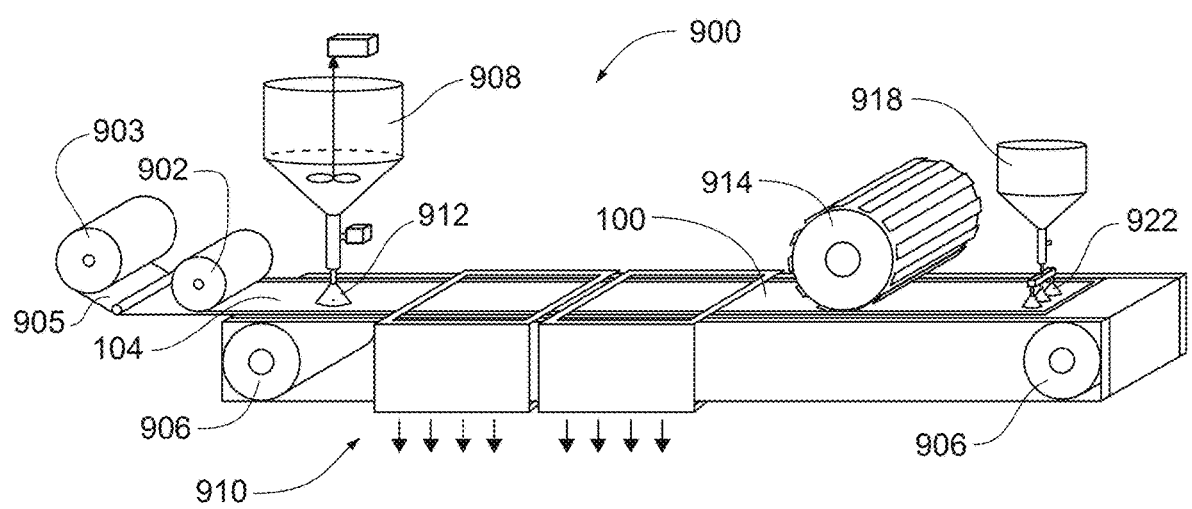
FIG. 9 shows a perspective view of an apparatus for manufacturing the nanocellulose composite sheet of FIG. 1A according to one embodiment of the present invention.

FIG. 9 is a perspective view of an apparatus 900 for manufacture of the nanocellulose composite sheet, comprising a moisturized nanocellulose material and a fabric, where the moisturized nanocellulose material and the fabric are bonded by mechanical adhesion. In different embodiments, the fabric is a woven or a non-woven fabric. The apparatus 900 is a continuous belt-driven production assembly.

The apparatus 900 comprises a storage for supplying the fabric 104, wherein the storage is designed as a first roller 902. Furthermore, the apparatus 900 comprises a suspension dispenser 908 for providing and dispersing a diluted nanocellulose suspension 912 onto the fabric 104, wherein the suspension dispenser 908 is designed as a continuous mixing hopper 908. The apparatus 900 further comprises a carrying device 906 for forwarding the fabric 104 to the continuous mixing hopper 908, wherein the carrying device 906 is designed as a conveyer belt 906.

Furthermore, the apparatus 900 comprises a dryer 910 for partially drying the diluted nanocellulose suspension 912 until the diluted nanocellulose suspension 912 is transformed into a moisturized nanocellulose material. In some embodiments, the dryer 910 is designed as a vacuum device 910 and/or a heat source. In some embodiments, a heat of the heat source is applied by an element selected from the group consisting of thermal convection, thermal conduction, thermal radiation, heat transfer by chemical conversion, chemical phase transition, and fluid advection. (Thermal radiation comprises infrared or microwave radiation. Chemical conversion comprises exothermic chemical reactions. Chemical phase transition comprises transitions from plasma to gas and vice versa, gas to liquid and vice versa, liquid to solid and vice versa. Fluid advection comprises mass transfer of heating or coolant fluid). However, in one embodiment, the dryer 910 is designed as a vacuum device 910.

In this embodiment, the apparatus 900 further comprises a cutter, such as a rotary die cutter 914, for cutting the nanocellulose composite sheet 100 into a desired shape and size.

The apparatus 900 may comprise a formulation dispenser 918 for infusing the nanocellulose composite sheet 100 with dermatological and/or cosmetic formulations 922, such as dermatological agents, drugs, active ingredients for the transfer of said dermatological and/or cosmetic formulations onto skin. In one embodiment, the formulation dispenser 918 is designed as a metered dose dispensing unit 918.

The apparatus 900 may comprise a second roller 903 for supplying a secondary inert filter 905 under the fabric 104.

Figure 10:
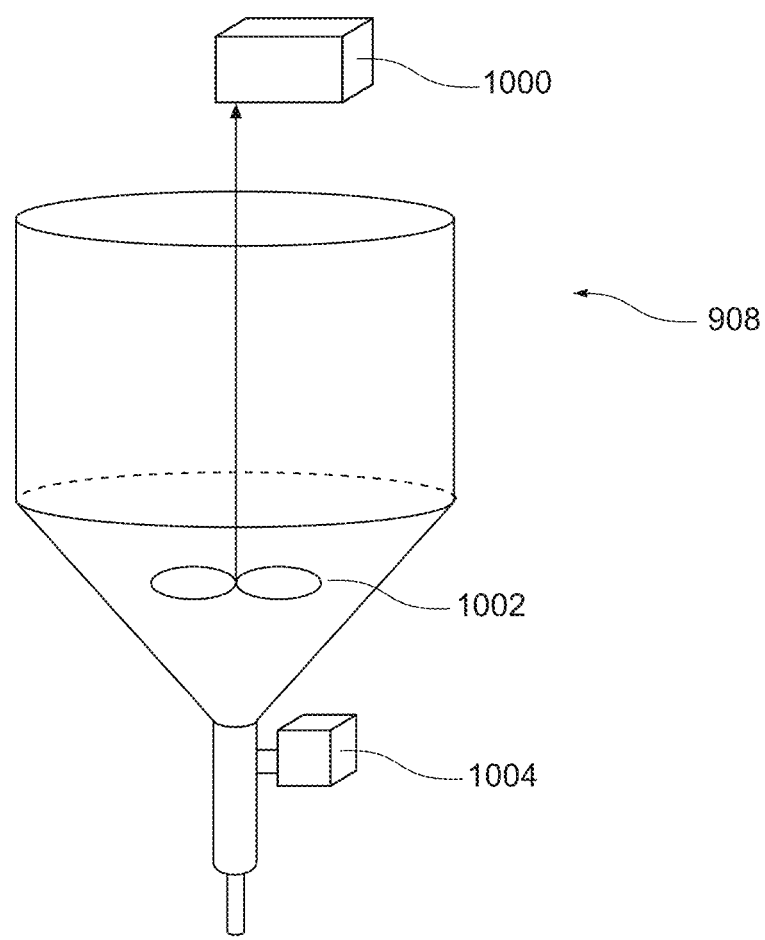
FIG. 10 shows a perspective view of the mixing hopper of FIG. 9 in greater detail, according to one embodiment of the present invention.

FIG. 10 shows a perspective view of the mixing hopper 908 of FIG. 9 in greater detail. The mixing hopper 908 comprises a hopper motor 1000 with rotary hopper blades 1002 for mixing the diluted nanocellulose suspension to maintain a continuous suspension, and a metered dispersion control unit 1004.

Figure 11:
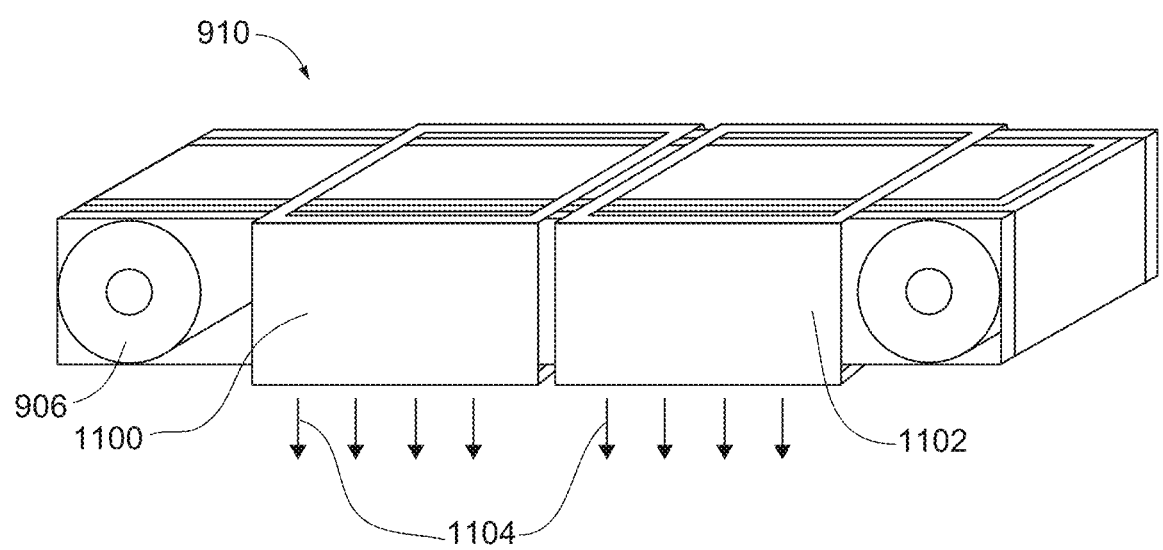
FIG. 11 shows a perspective view of the vacuum device of FIG. 9 in greater detail according to one embodiment of the present invention.

FIG. 11 shows a perspective view of the vacuum device 910 of FIG. 9 in greater detail. The vacuum device 910 comprises at least one suction box 1100, or a first and a second suction box 1100 and 1102, where the second suction box 1102 is independent from the first suction box 1100. A vacuum differential is depicted by arrows 1104, which show the direction of the suction produced in the first and second suction boxes 1100 and 1102. In various embodiments, one, two, or more independent suction boxes may be provided to provide more efficient drying.

Figure 12:
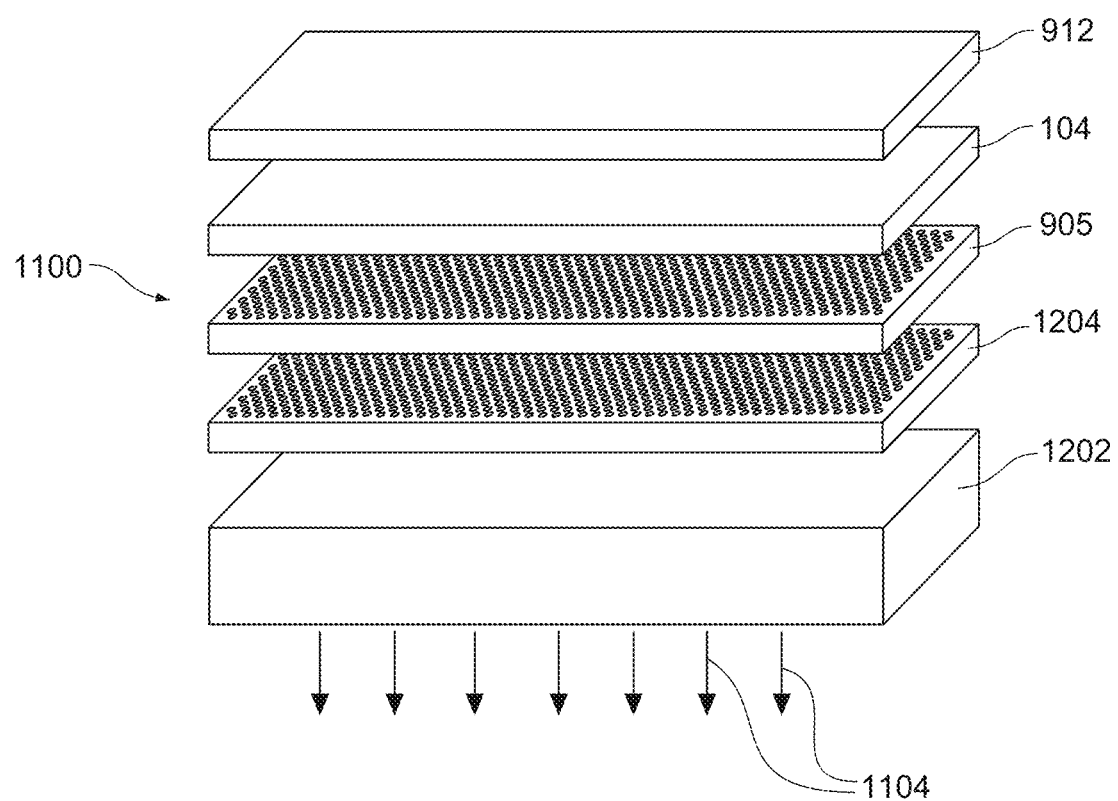
FIG. 12 shows an exploded perspective view of the first suction box of FIG. 11 according to one embodiment of the present invention.

FIG. 12 shows an exploded perspective view of the first suction box 1100 of FIG. 11. The first suction box 1100 comprises a suction box chamber 1202, where the vacuum differential is produced. The vacuum differential is depicted by the arrows 1104. A primary porous filter 1204 comprising plastic or metal may be placed inside the suction box chamber 1202, in a manner that the primary porous filter 1204 closes a downside of the suction box chamber 1202. The primary porous filter 1204 may comprise one or more openings to allow an airflow from an inside of the suction box chamber 1202 to an outside of the suction box chamber 1202.

The secondary inert filter 905 may be placed inside the suction box chamber 1202 on top of the primary porous filter 1204. The secondary inert filter 905 may also comprise one or more openings to allow an airflow from an inside of the suction box chamber 1202 to an outside of the suction box chamber 1202 through the primary porous filter 1204. The secondary inert filter 905 is provided by the second roller 920 (see FIG. 9 and description thereof).

Once the fabric 104 with the diluted nanocellulose suspension 912 on top is forwarded above the first suction box 1100, the vacuum differential dries the diluted nanocellulose suspension 912 until the moisturized nanocellulose material forms, and until the moisturized nanocellulose material and the fabric 104 are bonded by mechanical adhesion to form the nanocellulose composite sheet 100.

The primary porous filter 1204 and the secondary inert filter 905 support the fabric 104, once the fabric 104 is above the first suction box 1100. The primary porous filter 1204 and the secondary inert filter 905 are only in temporary contact with the fabric 104. Once the diluted nanocellulose suspension 912 forms the moisturized nanocellulose material, the primary porous filter 1204 and the secondary inert filter 905 are detached from the fabric 104.

The rate and extent of drying correlate with both the pressure of the vacuum differential and drying time. In some embodiments, the pressure is between 5 and 100 psi. In some other embodiments, the pressure may be above 1000 psi. The higher the pressure, the shorter the drying time to partially dry the diluted nanocellulose suspension 912 to the moisturized nanocellulose material.

The first suction box 1100 may increase a pressure with a gradient across the diluted nanocellulose suspension 912 and exerts a low-pressure vacuum differential, e.g. 5 psi (pounds per square inch). The primary porous filter 1204 and the secondary inert filter 905 may incrementally increase vacuum filtration pressure, for example, from 10 to 20 psi, and from 20 to 50 psi. The pressure of the vacuum differential can be a negative pressure or a positive pressure. In case of a negative pressure, air is pulled through the first suction box 1100 according to the arrows 1210. In case of a positive pressure, the air pushes through first suction box 1100.

The first suction box 1100 may be designed to also apply heat to the diluted nanocellulose suspension 912 to expedite the drying process through increase of vaporization. Drying time therefore decreases as temperature increases.

The vacuum differential may be applied to the diluted nanocellulose suspension 912 in one or more timed intervals. In this embodiment, the timed intervals are punctuated by timed intermissions of the vacuum differential. The application of the vacuum differential to the diluted nanocellulose suspension 912 in timed intervals can be performed in addition to the heat application to the diluted nanocellulose suspension 912.

The same configuration and procedures apply to the second suction box 1102 of FIG. 11.

Drying Time and Fluid Absorption of the Nanocellulose Composite Sheet

Figure 13:
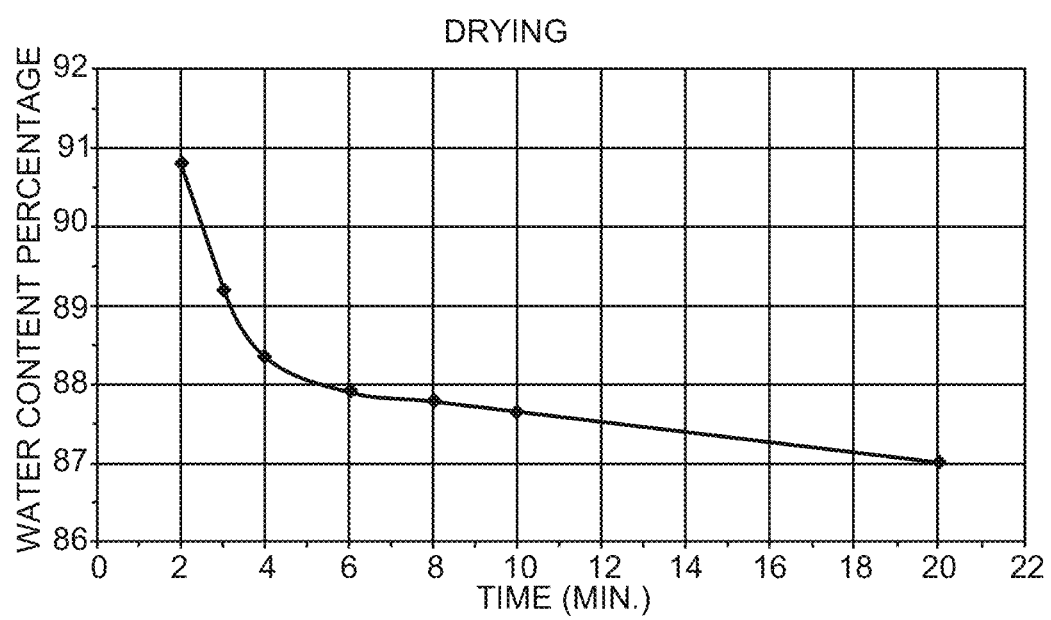
FIG. 13 shows a graph showing time-dependent drying of the diluted nanocellulose suspension given as measured water content against drying time during the production of the nanocellulose composite sheet according to one embodiment of the present invention.

FIG. 13 is a graph showing a time-dependent drying of the diluted nanocellulose suspension, according to some embodiments of the present invention. The graph shows a measured water content of the diluted nanocellulose suspension against time during the manufacture of the nanocellulose composite sheet. After 5 minutes of drying, the water content decreases to 88 weight %, and after 20 minutes of drying the water content decreases to 87 weight %.

Figure 14:
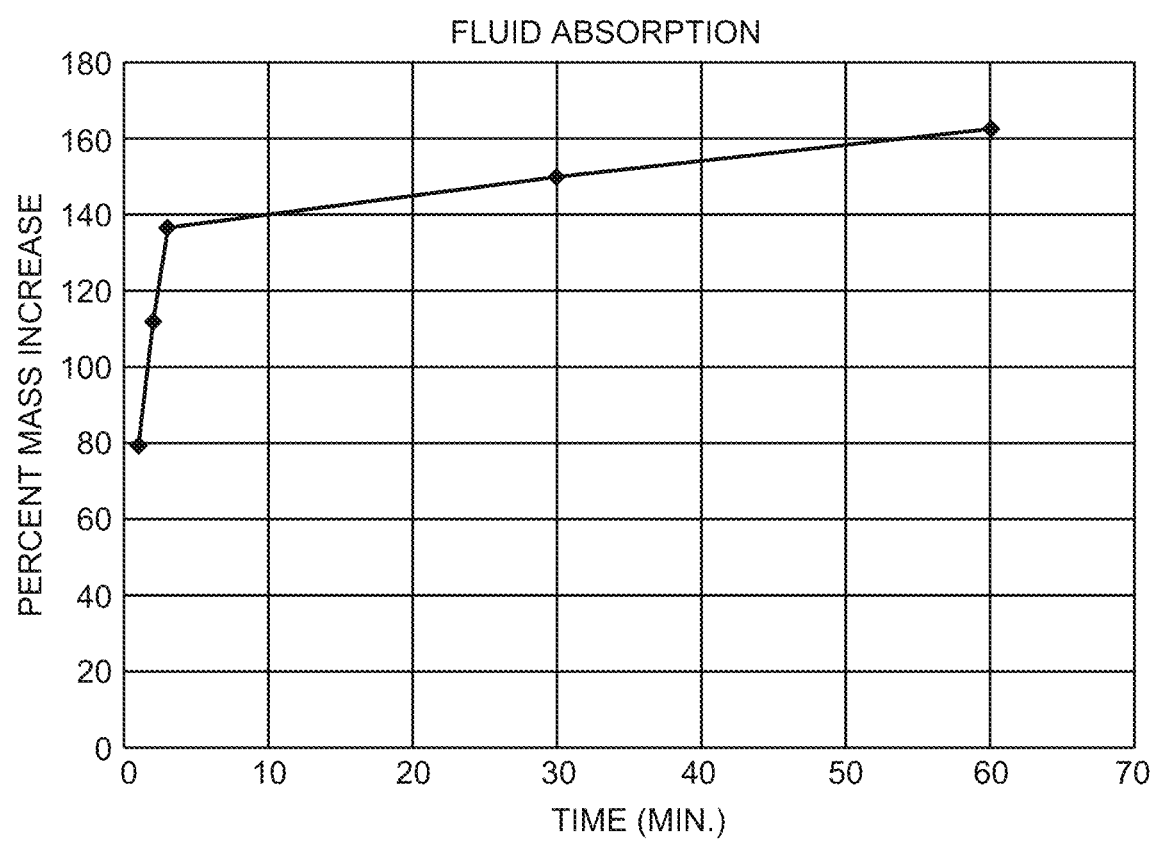
FIG. 14 shows a graph showing a time dependent fluid absorption capacity of an illustrative nanocellulose composite sheet made according to one embodiment of the present invention.

FIG. 14 is a graph showing an exemplary fluid absorption capability of an illustrative nanocellulose composite sheet made according to one embodiment of the present invention. The maximum fluid absorption for the illustrative nanocellulose composite sheet is shown in FIG. 14 as mass increase of the nanocellulose composite sheet, against time the nanocellulose composite sheet is exposed to a fluid. After only a few minutes, the maximum fluid absorption of the nanocellulose composite sheet may reach about 140 weight % of the nanocellulose composite sheet. And after 60 minutes, the maximum fluid absorption of the nanocellulose composite sheet may reach about 160 weight % of the nanocellulose composite sheet. FIG. 14 shows that when used for a dermatological application, the illustrative nanocellulose composite sheet can absorb up to 140 weight % of its own weight within a short period of time.

Alternative Embodiments

Some other alternative and illustrative embodiments of the present invention are described next. These alternative embodiments are not intended to limit the scope of the present invention or its application or uses.

One embodiment of the present invention is a method of manufacturing a nanocellulose composite sheet comprising a moisturized nanocellulose material composited with a non-woven fabric, the method comprising providing a purified nanocellulose aqueous gel; forming a diluted nanocellulose suspension; introducing the diluted nanocellulose suspension into a continuous mixing metered dispensing system; dispersing the diluted nanocellulose suspension into a sheet-forming filtration apparatus; applying a vacuum differential to partially dehydrate and layer the diluted nanocellulose suspension onto the non-woven fabric to form the nanocellulose composite sheet; and die cutting the nanocellulose composite sheet into specific shapes designed for placement on various skin and body areas of intended use to form the nanocellulose composite sheet.

In some embodiments, the method further comprises applying a flexible non-woven protective covering to the nanocellulose composite sheet.

In some embodiments, the method further comprises folding the nanocellulose composite sheet and packaging the nanocellulose composite sheet for distribution.

In some embodiments, the purified nanocellulose aqueous gel comprises nanocellulose selected from the group consisting of cellulose nanofibrils and cellulose nanocrystals.

In some embodiments, the diluted nanocellulose suspension has a nanocellulose concentration between 0.1 weight % to 3 weight %.

In some embodiments, the nanocellulose composite sheet has a nanocellulose concentration between 5 weight % to 25 weight %.

In some embodiments, the nanocellulose composite sheet is a standalone medical device.

In some embodiments, the nanocellulose composite sheet is a standalone cosmetic or dermatological hydrating or moisturizing device.

In some embodiments, the method further comprises infusing the composite sheet material with a solution of dermatologically active agents tailored to a specific dermatological purpose using a metered dosing system.

In some embodiments, the composite sheet material is infused with specific dermatological agents, drugs, and/or active ingredients tailored to specific medical indications.

In some embodiments, the composite sheet material is infused with selected dermatological and/or cosmetic formulations designed for specific dermatological and/or cosmetic purposes, and for the transfer of said selected dermatological and/or cosmetic formulations' ingredients from the nanocellulose composite sheet onto skin at an intended area of use.

In some embodiments, the non-woven fabric is selected from the group consisting of a synthetic fabric, a semi-synthetic fabric, and a non-synthetic fabric.

In some embodiments, the composite sheet material is supported by a secondary inert filter during the applying the vacuum differential.

In some embodiments, the method further comprises using a non-woven viscose fabric with a grammage between 35 and 45 gsm (g/m$^2$) non-woven viscose fabric and a final relative mass percentage of approximately 4 weight % CNF (carbon nanofiber) in the composite sheet material to yield the composite sheet material with a tensile strength of approximately 1.17 N/mm$^2$±0.25 N/mm$^2$.

Yet another embodiment of the present invention is a nanocellulose composite sheet comprising a moisturized nanocellulose sheet composited with a non-woven fabric, the nanocellulose composite sheet made by a process comprising providing a purified nanocellulose aqueous gel; forming a diluted nanocellulose suspension; introducing the diluted nanocellulose suspension into a continuous mixing metered dispensing system; dispersing the diluted nanocellulose suspension into a sheet-forming filtration apparatus; applying a vacuum differential to partially dehydrate and layer the diluted nanocellulose suspension onto a non-woven fabric to form the nanocellulose composite sheet; and die cutting the nanocellulose composite sheet into specific shapes designed for placement on various skin and body areas of intended use to form the nanocellulose composite sheet.

In some embodiments, the process further comprises applying a flexible non-woven protective covering to the nanocellulose composite sheet.

In some embodiments, the process further comprises folding the nanocellulose composite sheet and packaging for distribution.

In some embodiments, the purified nanocellulose aqueous gel comprises nanocellulose selected from the group consisting of cellulose nanofibrils and cellulose nanocrystals.

In some embodiments, the diluted nanocellulose suspension has a nanocellulose concentration between 0.1 weight % to 3 weight %.

In some embodiments, the nanocellulose composite sheet has a nanocellulose concentration between 5 weight % to 25 weight %.

In some embodiments, the nanocellulose composite sheet is a standalone medical device.

In some embodiments, the nanocellulose composite sheet is a standalone cosmetic or dermatological hydrating or moisturizing device.

In some embodiments, the process further comprises infusing the composite sheet material with a solution of dermatologically active agents tailored to a specific dermatological purpose using a metered dosing system.

In some embodiments, the composite sheet material is infused with specific dermatological agents, drugs, and/or active ingredients tailored to specific medical indications.

In some embodiments, the composite sheet material is infused with selected dermatological and/or cosmetic formulations designed for specific dermatological and/or cosmetic purposes, and for the transfer of said selected dermatological and/or cosmetic formulations' ingredients from the nanocellulose composite sheet onto skin at an intended area of use.

In some embodiments, the non-woven fabric is selected from the group consisting of a synthetic fabric, a semi-synthetic fabric, and a non-synthetic fabric.

In some embodiments, the composite sheet material is supported by a secondary inert filter during the applying the vacuum differential.

In some embodiments, the process further comprises using a non-woven viscose fabric with a grammage between 35 and 45 gsm (g/m$^2$) non-woven viscose fabric and a final relative mass percentage of approximately 4 weight % CNF (carbon nanofiber) in the composite sheet material to yield the composite sheet material with a tensile strength of approximately 1.17 N/mm$^2$±0.25 N/mm$^2$.

Yet another embodiment of the present invention is an apparatus for manufacturing a nanocellulose composite sheet comprising a moisturized nanocellulose sheet composited with a non-woven fabric, the apparatus comprising a roller for supplying the non-woven fabric; a conveyer belt system for driving the non-woven fabric down an assembly line; a mixing hopper for supplying a diluted nanocellulose suspension onto the non-woven fabric; at least a first vacuum suction box for applying vacuum to the non-woven fabric and the diluted nanocellulose suspension to produce a composite sheet material; and a die cutter for cutting the composite sheet material into a desired shape and size to form the nanocellulose composite sheet.

In some embodiments, the apparatus further comprises at least a second independent suction box for applying vacuum to the non-woven fabric and the diluted nanocellulose suspension.

In some embodiments, the first vacuum suction box comprises a primary porous filter and a suction box chamber for applying vacuum.

In some embodiments, the mixing hopper comprises a hopper motor, a continuous mixing hopper, and a metered dispersion control unit.

In some embodiments, the apparatus further comprises a metered dose dispensing unit for infusing the composite sheet material with a solution of dermatologically active agents tailored to a specific dermatological purpose.

In some embodiments, the composite sheet material is infused with specific dermatological agents, drugs, active ingredients, and/or cosmetic ingredients.

In some embodiments, the apparatus further comprises a second roller for supplying a secondary inert filter under the non-woven fabric on the assembly line.

Yet another embodiment of the present invention is a nanocellulose composite sheet, comprising a moisturized nanocellulose sheet composited with a non-woven fabric.

In some embodiments, the nanocellulose composite sheet further comprises a flexible non-woven protective covering on the nanocellulose composite sheet.

In some embodiments, the moisturized nanocellulose sheet comprises nanocellulose selected from the group consisting of cellulose nanofibrils and cellulose nanocrystals.

In some embodiments, the nanocellulose composite sheet has a nanocellulose concentration between 5 weight % to 25 weight %.

In some embodiments, the nanocellulose composite sheet is a standalone medical device.

In some embodiments, the nanocellulose composite sheet is a standalone cosmetic or dermatological hydrating or moisturizing device.

In some embodiments, the moisturized nanocellulose sheet is infused with a solution of dermatologically active agents tailored to a specific dermatological purpose.

In some embodiments, the moisturized nanocellulose sheet is infused with specific dermatological agents, drugs, and/or active ingredients tailored to specific medical indications.

In some embodiments, the moisturized nanocellulose sheet is infused with selected dermatological and/or cosmetic formulations designed for specific dermatological and/or cosmetic purposes, and for the transfer of said selected dermatological and/or cosmetic formulations' ingredients from the nanocellulose composite sheet onto skin at an intended area of use.

In some embodiments, the non-woven fabric is selected from the group consisting of a synthetic fabric, a semi-synthetic fabric, and a non-synthetic fabric.

In some embodiments, the fabric is a non-woven viscose fabric having a grammage between 35 and 45 gsm (g/m$^2$).

In some embodiments, the nanocellulose composite sheet has a final relative mass percentage of approximately 4 weight % CNF (carbon nanofiber).

In some embodiments, the nanocellulose composite sheet has a tensile strength of approximately 1.17 N/mm$^2$±0.25 N/mm$^2$.

CONCLUSIONS

One of ordinary skill in the art knows that the use cases, structures, schematics, and flow diagrams may be performed in other orders or combinations, but the inventive concept of the present invention remains without departing from the broader scope of the invention. Every embodiment may be unique, and steps may be either shortened or lengthened, overlapped with the other steps, postponed, delayed, and continued after a time gap, such that every use case and application can be accommodated to practice the methods of the present invention.

Although the present invention has been described with reference to specific exemplary embodiments, it will be evident that various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A two-layer nanocellulose composite sheet, comprising:
   a first layer comprising a first moisturized nanocellulose material; and
   a second layer comprising a non-woven viscose fabric, wherein the non-woven viscose fabric comprises a network of fibers made of at least a second material different from the first moisturized nanocellulose material, and wherein a surface of the first layer is mechanically adhered to a surface of the second layer.

2. The two-layer nanocellulose composite sheet of claim 1,
   wherein the first moisturized nanocellulose material comprises nanocellulose and water, wherein the nanocellulose is between 10 and 12 weight % of the nanocellulose composite sheet, and wherein the water is between 76 and 80 weight % of the nanocellulose composite sheet.

3. The two-layer nanocellulose composite sheet of claim 1, wherein the non-woven viscose fabric is between 10 and 12 weight % of the nanocellulose composite sheet.

4. The two-layer nanocellulose composite sheet of claim 1, wherein the first moisturized nanocellulose material comprises at least one element selected from the group consisting of cellulose nanocrystals, cellulose nanofibers, nanofibrillated cellulose, and bacterial nanocellulose.

5. The two-layer nanocellulose composite sheet of claim 1, wherein the first moisturized nanocellulose material comprises a plurality of cellulose fibrils with a width between 5 and 20 nanometers and a length between 1 and 10 micrometers.

6. The two-layer nanocellulose composite sheet of claim 1, wherein the first moisturized nanocellulose material comprises crystalline and rigid nanoparticles.

7. The two-layer nanocellulose composite sheet of claim 6, wherein the crystalline and rigid nanoparticles have a length between 100 and 1,000 nanometers.

8. The two-layer nanocellulose composite sheet of claim 1, wherein the non-woven viscose fabric has a grammage between 35 and 45 gsm (g/m$^2$).

9. The two-layer nanocellulose composite sheet of claim 1, wherein the first moisturized nanocellulose material has a nanocellulose concentration between 5 weight % to 25 weight %.

10. The two-layer nanocellulose composite sheet of claim 1, wherein the first moisturized nanocellulose material is a hydrated nanocellulose material.

11. The two-layer nanocellulose composite sheet of claim 1, further comprising:

a flexible non-woven protective covering.

* * * * *